US008702801B2

(12) United States Patent
Linares

(10) Patent No.: US 8,702,801 B2
(45) Date of Patent: Apr. 22, 2014

(54) ARTIFICIAL WEAR RESISTANT PLUG FOR MOUNTING TO EXISTING JOINT BONE

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 63 days.

(21) Appl. No.: 12/919,242

(22) PCT Filed: Apr. 24, 2009

(86) PCT No.: PCT/US2009/041627
§ 371 (c)(1),
(2), (4) Date: Aug. 25, 2010

(87) PCT Pub. No.: WO2009/108960
PCT Pub. Date: Sep. 3, 2009

(65) Prior Publication Data
US 2011/0035012 A1     Feb. 10, 2011

Related U.S. Application Data

(60) Provisional application No. 61/031,192, filed on Feb. 25, 2008.

(51) Int. Cl.
*A61F 2/38*       (2006.01)
(52) U.S. Cl.
USPC ..................................... 623/20.15
(58) Field of Classification Search
USPC ................. 623/13.12–13.19, 20.14–20.36
See application file for complete search history.

(56) References Cited

U.S. PATENT DOCUMENTS

| 2,667,644 | A |   | 2/1954  | Johnson |
|-----------|---|---|---------|---------|
| 3,651,521 | A |   | 3/1972  | Devas |
| 3,798,679 | A |   | 3/1974  | Ewald |
| 3,875,594 | A |   | 4/1975  | Swanson |
| 3,964,106 | A |   | 6/1976  | Hutter, Jr. et al. |
| 4,215,439 | A |   | 8/1980  | Gold et al. |
| 4,231,122 | A |   | 11/1980 | Koeneman |
| 4,328,593 | A | * | 5/1982  | Sutter et al. ............ 623/23.42 |
| 4,367,562 | A |   | 1/1983  | Gauthier et al. |
| 4,538,305 | A |   | 9/1985  | Engelbrecht et al. |
| 4,714,477 | A |   | 12/1987 | Fichera et al. |
| 4,950,298 | A | * | 8/1990  | Gustilo et al. ............ 623/20.15 |
| 4,964,868 | A |   | 10/1990 | Bloebaum |
| 4,990,161 | A |   | 2/1991  | Kampner |
| 5,007,934 | A |   | 4/1991  | Stone |
| 5,021,061 | A |   | 6/1991  | Wevers et al. |

(Continued)

FOREIGN PATENT DOCUMENTS

JP          07116184 A       5/1995

*Primary Examiner* — David Isabella
*Assistant Examiner* — Ann Schillinger
(74) *Attorney, Agent, or Firm* — Gifford, Krass, Sprinkle, Anderson & Citkowski, P.C.; Douglas J. McEvoy

(57) ABSTRACT

An artificial and wear-resistant plug mounted to an existing bone associated with a joint structure and which includes a three dimensional and composite platicized material. An end surface of an existing bone is reconditioned in preparation for engagement of the plug thereto and in order to define a reconditioned artificial wear surface. In a preferred application, a pair end mounted plugs are arranged in opposing fashion between first and second bones and respectively define a male receiving end and a female socket. A lubricant retaining and cartilage defining exterior layer is applied to one or both of opposing surfaces of the plugs.

1 Claim, 13 Drawing Sheets

(56) References Cited

U.S. PATENT DOCUMENTS

| | | | |
|---|---|---|---|
| 5,092,898 A | 3/1992 | Bekki et al. | |
| 5,171,325 A | 12/1992 | Aulie | |
| 5,197,987 A | 3/1993 | Koch et al. | |
| 5,389,107 A | 2/1995 | Nassar et al. | |
| 5,462,362 A | 10/1995 | Yuhta et al. | |
| 5,509,934 A | 4/1996 | Cohen | |
| 5,553,476 A | 9/1996 | Oehy et al. | |
| 5,571,193 A | 11/1996 | Kampner | |
| 5,593,445 A | 1/1997 | Waits | |
| 5,645,601 A | 7/1997 | Pope et al. | |
| 5,662,158 A | 9/1997 | Caldarise | |
| 5,676,702 A | 10/1997 | Ratron et al. | |
| 5,702,476 A | 12/1997 | Limacher et al. | |
| 5,728,175 A | 3/1998 | Rincoe | |
| 5,800,566 A | 9/1998 | Gramnas | |
| 5,879,406 A | 3/1999 | Lilley | |
| 5,916,269 A | 6/1999 | Serbousek et al. | |
| 5,921,358 A | 7/1999 | Gramnas et al. | |
| 6,045,581 A | 4/2000 | Burkinshaw | |
| 6,165,223 A | 12/2000 | Metzger et al. | |
| 6,398,815 B1 | 6/2002 | Pope et al. | |
| 6,627,141 B2 | 9/2003 | McNulty et al. | |
| 6,660,040 B2 | 12/2003 | Chan et al. | |
| 6,692,679 B1 | 2/2004 | McNulty et al. | |
| 6,723,102 B2 | 4/2004 | Johnson et al. | |
| 6,800,298 B1 | 10/2004 | Burdick et al. | |
| 6,800,670 B2 | 10/2004 | Shen et al. | |
| 6,811,568 B2 | 11/2004 | Minamikawa | |
| 6,818,172 B2 | 11/2004 | King et al. | |
| 6,866,683 B2 * | 3/2005 | Gerbec et al. | 623/18.11 |
| 6,866,685 B2 | 3/2005 | Chan et al. | |
| 6,962,607 B2 | 11/2005 | Gundlapalli et al. | |
| 7,044,983 B1 | 5/2006 | Cheng et al. | |
| 7,066,958 B2 | 6/2006 | Ferree | |
| 7,077,867 B1 | 7/2006 | Pope et al. | |
| 7,087,091 B1 | 8/2006 | Chen et al. | |
| 7,109,181 B2 | 9/2006 | Cowlen et al. | |
| 7,148,209 B2 | 12/2006 | Hoemann et al. | |
| 7,175,666 B2 | 2/2007 | Yao | |
| 7,179,298 B2 | 2/2007 | Greenlee | |
| 7,186,364 B2 | 3/2007 | King et al. | |
| 7,331,995 B2 | 2/2008 | Eisermann et al. | |
| 7,384,430 B2 | 6/2008 | Greer et al. | |
| 7,578,851 B2 | 8/2009 | Dong et al. | |
| 7,771,485 B2 | 8/2010 | Grundei | |
| 7,780,738 B2 | 8/2010 | Khandkar et al. | |
| 2002/0183845 A1 | 12/2002 | Mansmann | |
| 2003/0055508 A1 * | 3/2003 | Metzger et al. | 623/20.15 |
| 2003/0065401 A1 | 4/2003 | Amrich et al. | |
| 2003/0114935 A1 | 6/2003 | Chan et al. | |
| 2003/0216669 A1 | 11/2003 | Lang et al. | |
| 2004/0024460 A1 | 2/2004 | Ferree | |
| 2004/0068322 A1 | 4/2004 | Ferree | |
| 2005/0055100 A1 | 3/2005 | Lewis et al. | |
| 2005/0171604 A1 | 8/2005 | Michalow | |
| 2005/0192672 A1 | 9/2005 | Wyss et al. | |
| 2005/0192674 A1 | 9/2005 | Ferree | |
| 2005/0287187 A1 | 12/2005 | Mansmann | |
| 2006/0015186 A1 | 1/2006 | Isaac | |
| 2007/0179613 A1 | 8/2007 | Heinz | |
| 2007/0287027 A1 | 12/2007 | Justin et al. | |
| 2008/0033567 A1 | 2/2008 | Stchur | |
| 2008/0288081 A1 | 11/2008 | Scrafton et al. | |
| 2009/0076605 A1 | 3/2009 | Linares | |
| 2009/0125108 A1 | 5/2009 | Linares | |

* cited by examiner

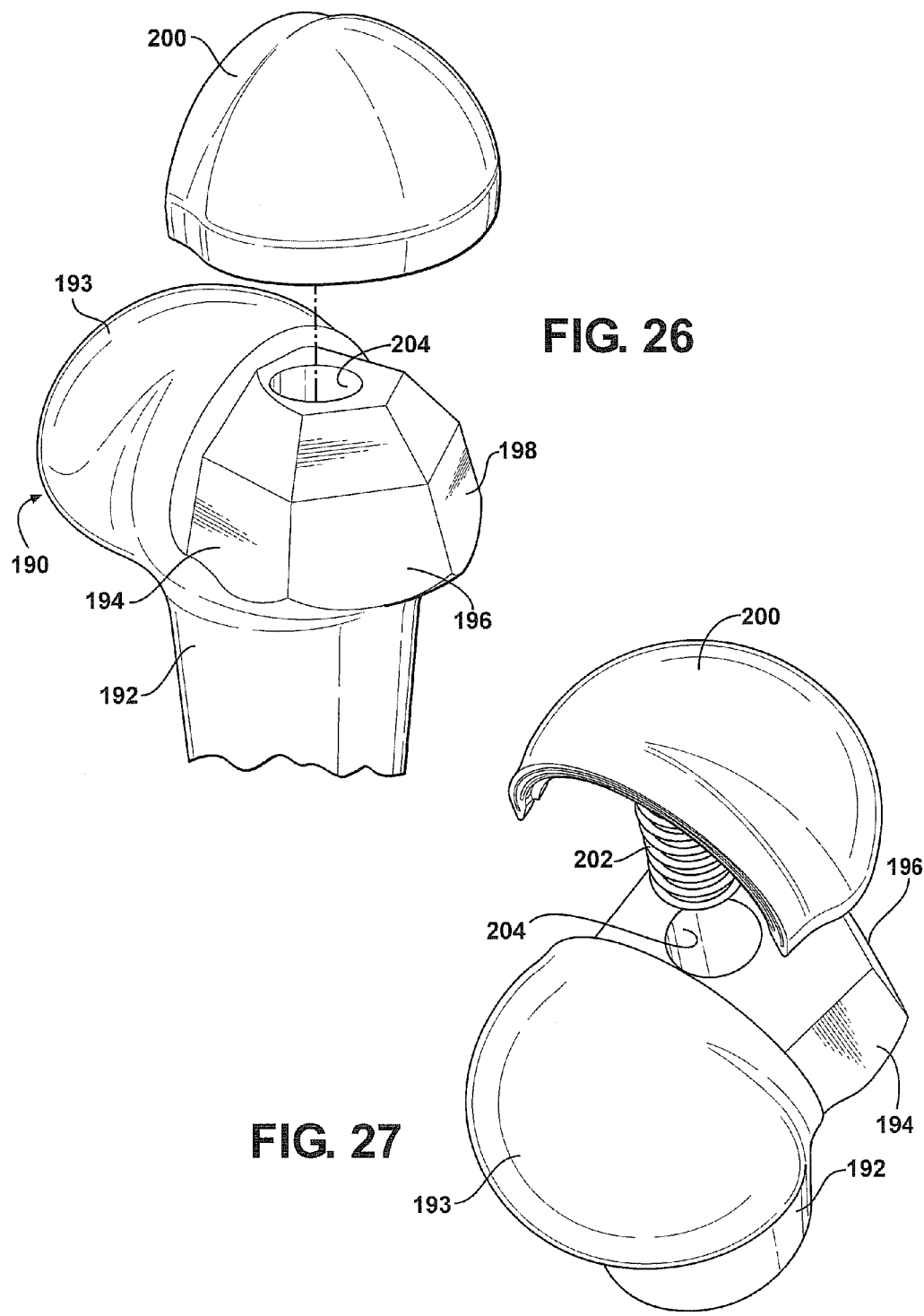

ARTIFICIAL WEAR RESISTANT PLUG FOR MOUNTING TO EXISTING JOINT BONE

CROSS-REFERENCE TO RELATED APPLICATIONS

This Application claims the benefit of U.S. Provisional Application 61/031,192 filed on Feb. 25, 2008.

FIELD OF THE INVENTION

The present invention relates generally to retrofit joint assemblies associated with existing bone structure. More specifically, the present invention discloses an artificial and wear-resistant plug adapted for mounting to an opposing end face of at least one existing and joint defined bone and in order to provide a retrofit knee assembly associated with reduce discomfort and recovery time.

BACKGROUND OF THE INVENTION

The prior art is documented with examples of implant devices and assemblies, such typically being retrofit applied to existing joints. Representative examples of known implant devices and assemblies include, among others, the implant device and method of manufacture set forth in Philipp, U.S. Publication No. 2008/0195216 and which teaches a knee implant with first and second component surfaces. U.S. Pat. No. 7,291,169, issued to Hodorek, teaches a cartilage implant for replacing a portion of the cartilage adjacent to a skeletal joint.

Additional examples of joint prosthesis include the implant of Buscheer, US 2008/0071381 which teaches an implant joint with a micro-rough bearing surface formed by sintering. Scott 2008/0114459 discloses a prosthesis implanted within a bone and including a shell and inter-fitting liner.

SUMMARY OF THE PRESENT INVENTION

The present invention discloses an artificial and wear-resistant plug mounted to an existing bone associated with a joint structure and which includes a three dimensional and composite plasticized material. An end surface of an existing bone is reconditioned in preparation for engagement of the plug thereto and in order to define a reconditioned artificial wear surface. In a preferred application, a pair end mounted plugs are arranged in opposing fashion between first and second bones and respectively define a male receiving end and a female socket. A lubricant retaining and cartilage defining exterior layer is applied to one or both of opposing surfaces of the plugs.

Other features include a plurality of lubricant communicating channels associated with at least one of the plug and lubricant communicating layers. The polymeric insert plug further exhibits an integrally defined and interiorly extending root structure for being secured to a mating and associated interiorly machined surface of the bone. An injected expansion plastic is employed for filling a cavity established between said plug root structure and a cored recess of the bone.

At least one of the joint establishing and opposing implant plugs is secured through cutting, notching or abrasive resurfacing of an associated bone end surface prior to surface engagement thereto of at least one of the plasticized materials according to a specified shape and at a co-acting location with an opposing bone. The surface attached materials further can include clip portions which are secured to the bone end surfaces, via reverse face extending fasteners seating within interiorly machined drill hole locations associated with the bone ends.

In one variant, the plasticized insert material can include a miniaturized, flexible and depth-wise apertured wear disc placed in localized inter-disposed fashion between selected coacting surfaces associated with first and second joint establishing bone surface, the flexible wear disc further being constructed of a soft cushioning plastic. The composite plasticized material may also include a substantially keystone shaped insert configured for localized engagement with a selected joint end face location.

The insert may further exhibit under surface roughening such that, upon installing the insert into a machined end face of the bone in contact with the bone marrow, new bone adhesion is promoted. The composite plastic material may also incorporate a plastic insert with recess mounting studs, these securing at first and second abrading joint surface locations associated with the bone.

Additional variants include a whole or partial joint established between male projecting/extending and female/cup-shaped receiving end secured implants. The male and female defined ends are configured to mimic the normal interaction of surfaces corresponding to such as knee joint, as well as in additional applications to such as elbow and hip joints.

In addition to the male/female configured ends, the assembly may also include interconnecting/transitioning stem portions, these connecting at a first end to a rear surface of either male or female implant. The stem portions are interiorly hollowed with an open communicating end and are configured to seat within the hollow interior of the sectioned bone end. Surface area increasing portions, such as various types of keyed portions, are configured upon the open inner surfaces of the stem portions, these promoting the increase in natural bone growth and adhesion.

BRIEF DESCRIPTION OF THE DRAWINGS

Reference will now be made to the attached drawings, when read in combination with the following detailed description, wherein like reference numerals refer to like parts throughout the several views, and in which:

FIG. 26 is a perspective illustration of a male portion associated with a partial joint assembly according to a further preferred embodiment;

FIG. 27 is a further rotated perspective of FIG. 26 and illustrating the threaded mounting shaft associated with the surface secured implant cap for adhesive engagement to a combined substrate and stem supporting portion;

DETAILED DESCRIPTION OF THE PREFERRED EMBODIMENTS

Figure 1:
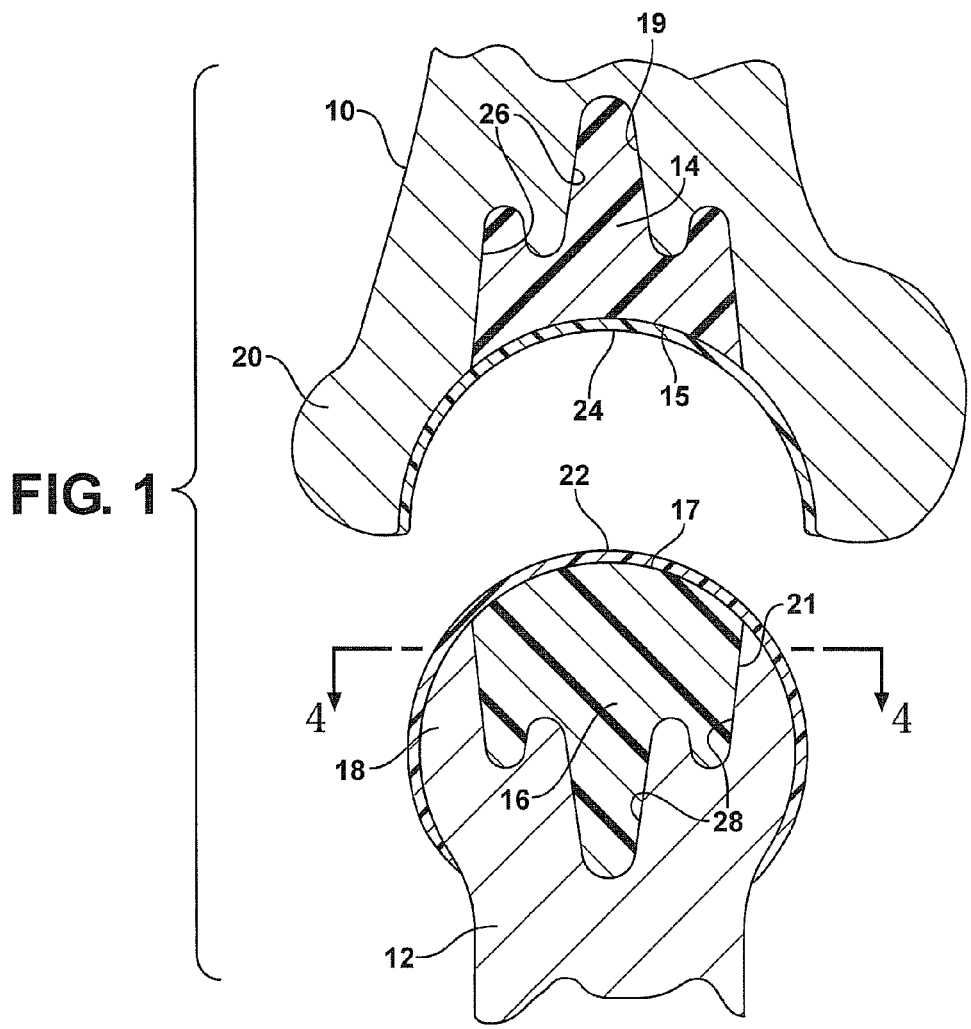
FIG. 1 is an exploded view of a selected joint assembly with first and second existing bones, and which have been retrofit designed to incorporate an end-supported wear resistant plug within each of first bone receiver/ball and second bone socket locations, as well as the provision of exterior most and opposing cartilage lubricant surfaces associated with each plug or opposing joint defining surface.

Referring now to FIG. 1, an exploded view is shown of a retrofit joint assembly according to a first embodiment and which reconditions and repairs worn joints associated with natural bones. In particular, the present invention discloses associated articles, assemblies and methods for reconditioning, such as occurring in vivo within a patient and with the use of sophisticated medical drills and related tools, the worn ends of first and second bones and prior to installation of prosthetic joint implants which are much less invasive than previously known implant designs and which provide for dramatic increases in patient comfort and wear life.

As shown in FIG. 1, first 10 and second 12 existing bones are illustrated, these including typically natural bones but which are also envisioned to include artificial implants. The bones 10 and 12 are generally configured to establish a male (ball) and female (receiver) configuration, such as associated with a knee or hip joint.

As further shown, opposing and joint defining ends of each of the bones 10 and 12 have been retrofit designed to incorporate associated and end-supported wear resistant plugs, see respectively at 14 and 16, these being shown in installed fashion within each of a first bone receiver/ball portion 18 (associated with bone 12) and a second bone socket location 20 (associated with bone 14). The plugs 14 and 16 as shown each include a forward facing edge surface corresponding in configuration with either the outline of the male or female joint defining bone (see concave profile 15 of female plug 14 and convex profile 17 of male plug 16). The plugs 14 and 16 are further understood as being constructed from any of a multitude of different materials, such as including composite plastics and/or plastics entrained with metallic, ceramic or siliceous ingredients in order to increase their wear life and other properties.

Although not shown, it is understood that appropriate medical drills can be employed, such as again in vivo within the patient in the instance of reconditioning of existing joints, such drills including sophisticated bits and the like for creating a desired undercut pattern (see as subsequently illustrated and described at 26 and 28) for seating and securing (such as in a mechanical or adhesive mounting fashion) rear configured mounting surfaces (shown at 19 and 21, respectively) and corresponding to the mounted insert plugs 14 and 16.

Figure 2:
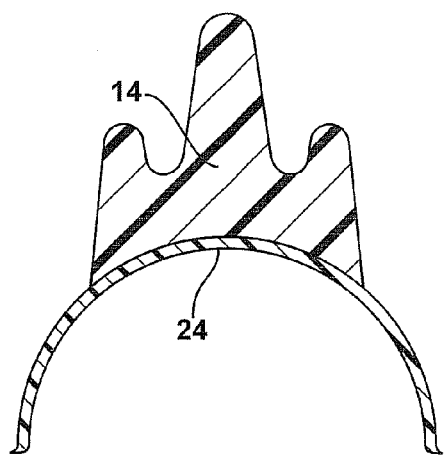
FIG. 2 is a sectional illustration showing a first end plug construction, and such as is associated with the upper bone in FIG. 1 and including the integral forming of the cartilage defined surface layer with the female associated insert plug.
Figure 3:
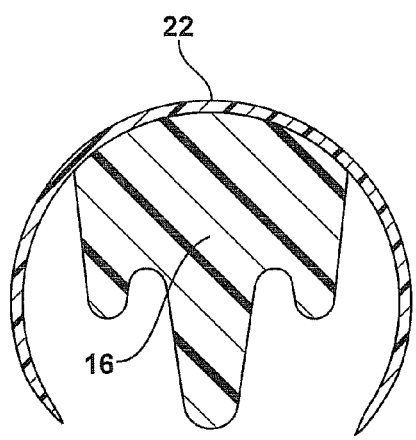
FIG. 3 is a sectional illustration of a second end plug construction, and such as is associated with the lower bone in FIG. 1 and including the integral forming of the cartilage defined surface layer with the male associated insert plug.

Also shown in FIG. 1 is the provision of exterior most and opposing cartilage-like covering or lubricant surfaces, see at 22 applied to ball portion 18 of male bone 12 and further at 24 applied to female receiver portion 20 of female bone 10. The cartilage/lubricant inducing surfaces 22 and 24 are typically installed in adhering fashion along a smooth concave/convex associated surface of the joint, such as a subsequent step after prior reconditioning of the bone end surfaces and subsequent installation of the plug shaped inserts 14 and 16. As shown in FIGS. 2 and 3, it is also envisioned that the plugs 14 and 16 and associated cartilage/lubricant defining surfaces can be provided in integrally forming fashion and for attachment in a single mounting operation to an end of a previously reconditioned bone.

As described, the lubricant surfaces 22 and 24 are also intended to mimic/replicate known cartilage surfaces not limited to Hyaline cartilage, which is a hard, translucent material rich in collagen and proteoglycan that, in addition to other known purposes, covers an end of bone to form the smooth articular joint surface. It is also known that bones grow via a hyaline cartilage intermediate, according to a process called Endochondral ossification. Additional known joint materials, such as ligaments and the like, are not illustrated through the several views however it is understood that appropriate natural and/or artificial ligaments are employed where needed and in order to establish a desired joint environment.

The several variants of the inventions disclosed herein address the concept of utilizing existing but damaged bones of a patient, which are retrofit modified by advanced machining/forming techniques in situ within the patient, and to which are secured the associated plugs 14 and 16 with associated lubricant providing cartilage surfaces 22 and 24. Such retrofit modification of the bones typically includes the coring out each opposing and end facing area in the associate joint establishing region, following which a previously designed and form fitting plug is anchored place, such as to both the male and female bone locations, and in a fashion which provides maximum frictionless wear support, while at the same time providing a maximum degree of flexibility.

The plugs, as each reference at 14 and 16 in FIGS. 2 and 3, are again constructed from any type of plasticized, or modified composite plasticized, material including any of a wide range of polymers not limited to urethanes, silicones, elastomers and the like. The plugs 14 and 16 each further illustrate a substantially root-like structure not unlike that of a tooth and which, upon coring the interior of each bone, see for example inwardly formed surfaces 26 associated with bone 10 and additional recessed surfaces 28 associated with bone 12, are matingly fixed in place through the application of such as fasteners, adhesives or the like and in order to recondition and re-establish the exterior facing and joint defining surfaces of the bones 10 and 12.

It is also envisioned that the plugs can be applied to either or both the male and female bone locations as shown in FIG. 1. The exterior lubricant inducing cartilage surfaces (again at 22 and 24) applied to the plugs 14 and 16 are further understood to communicate either natural or artificial/synthetic lubricants originating from the plugs (or such as from remote or interiorly located reservoirs) to the opposing surfaces of the cartilage layers. Additionally, and although not shown, it is again understood that ligaments and other connective structure is employed, such as including both naturally occurring ligament structure as well as the possible implantation of additional and synthetic ligaments including such as reinforced graphite in use with other synthetic materials, and in order to complete the desired joint structure.

Figure 4:
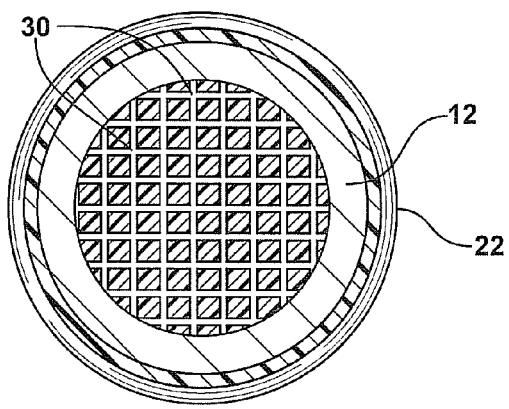
FIG. 4 is a modified end cutaway of a selected plug arrangement and illustrating such as a surface defined and grid-shaped pattern for communicating lubricant to the exteriorly defined and associated cartilage lubricant surface.

As further shown in FIG. 4, a representative illustration of a cartilage/lubricant defining surface is accomplished such as through the provision of a surface defined and grid-shaped pattern 30 for communicating lubricant to the exteriorly defined and associated cartilage lubricant surface, see for example lubricant surface 22 associated with plug 16 (and which is presented in partial cutaway for purposes of ease of illustration). The grid pattern 30 (which can also be incorporated into each of the plugs) operates to communicate lubricant (and such as which in addition to artificial lubricants can also include naturally occurring lubricant existing within the individual's natural bone structure) from the associated plug (e.g. again at 14 and 16) and into a rear communicating face of the cartilage defined lubricating layer 22 and 24.

It is also contemplated that the plurality of lubricant communicating channels can be associated with either or both of the plug and the over-molded lubricant communicating layers. In addition to the grid-shaped pattern disclosed at 30, other fluid communicating patterns or tracks will be described with reference to subsequent embodiments and which assist in establishing substantially frictionless and lubricated support between the joint defining surfaces.

Figure 5:
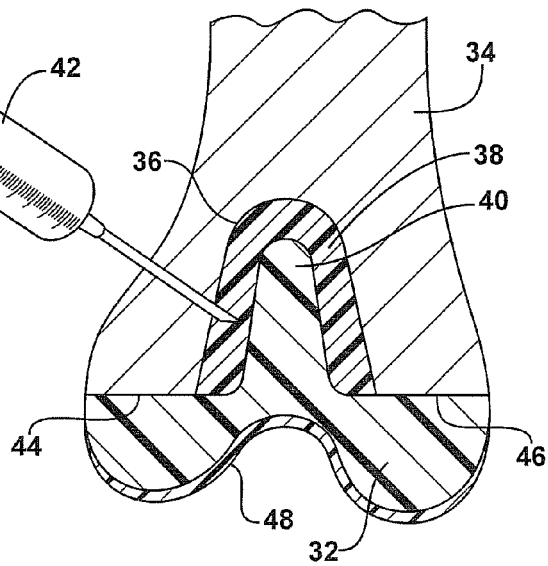
FIG. 5 is a plan view of a further version of plug shaped and attachable implant for retrofit attachment to an existing and end prepared bone.
Figure 6:
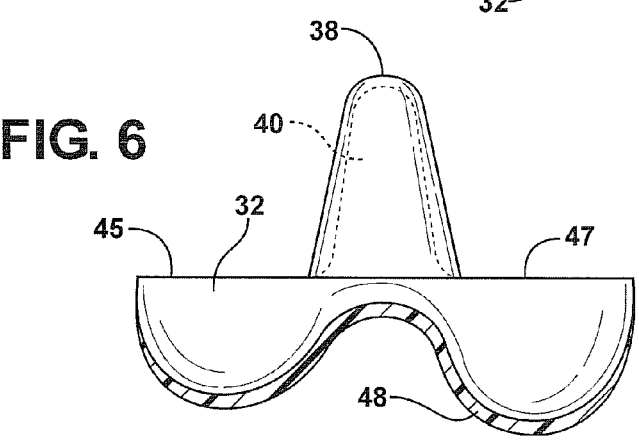
FIG. 6 is an illustration of the plug shaped implant shown in FIG. 5.

Referring now to FIG. 5, a plan view is shown of a further version of plug shaped and attachable implant 32 (see also separated illustration of the plug 32 in FIG. 6) for retrofit attachment to an existing and end prepared bone 34. As previously described, and prior to attachment of the plug implant 32, a damaged and joint established end of the bone 34 is reconditioned according to a desired medical procedure utilizing sophisticated drill and milling tools (and again typically while the associated bone remains in situ or in vivo within the patient).

Upon the establishment of the desired and reconditioned mounting surfaces associated with the bone end face, and such as upon pre-positioning of the implant 32 over the prepared bone end face (see at 36 in FIG. 5), an expansion plastic 38 (such as a two part reacting plastic with highly adhesive qualities) can be partially filled into the remaining void established between the cored out bone interior and a rearward most seating (or root supporting) portion 40 of the plug 32. As shown in FIG. 5, a syringe 42 and needle can be employed for penetrating through such as a pre-drilled or other access permitting location associated with the bone 34, and for (re) filling the void and, such as in combination with cement material applied to additional engaging surfaces (see at 44 and 46) associated with the conditioned end of the bone 34 and which seat against inner seating surfaces 45 and 47 (see again FIG. 6) of the plug 32, and which in combination fills the inner diameter of the machined/cored out bone 34 and permanently affixing the plug 32 to the reconditioned end of the bone. A suspension plastic lubricating material 48 (the equivalent of a cartilage layer) is secured to an exterior facing surface of the plug implant 32 and in order to establish a desired and substantially lubricated/frictionless relationship between the implant and an opposing bone joint (with or without end plug).

Figure 7:
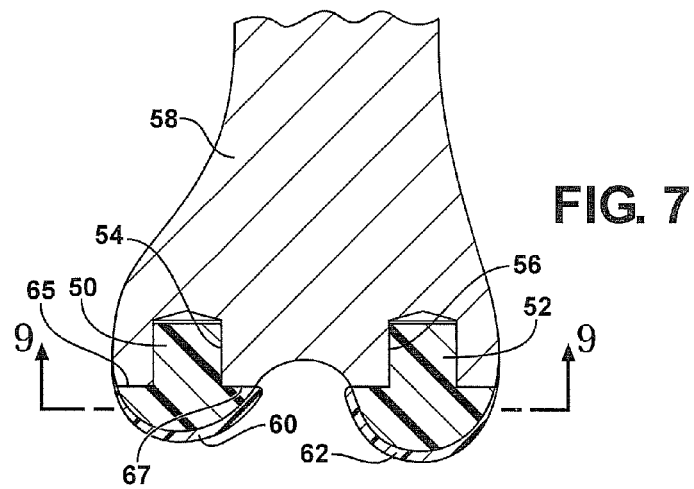
FIG. 7 is an illustration similar to FIG. 5 of a further example of first and second wear resistant plugs secured, via recess drill mountings, to projecting end locations of a selected bone.
Figure 8:
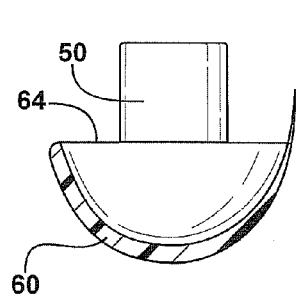
FIG. 8 is an enlarged illustration of a selected and wear resistant plug shown in FIG. 7.

Referring now to FIG. 7, a cutaway illustration is shown of a bone similar in shape to that previously shown in FIG. 5 and presenting a further example of first 50 and second 52 partial wear resistant plugs secured, such as via recess drilled or bored mountings (see interiorly cored end surfaces 54 and 56) proximate a pair of projecting end locations associated with a selected (e.g. typically natural) bone 58. A selected one of the plugs is illustrated in again at 50 in enlarged fashion in FIG. 8, and each of the plugs 50 and 52 again includes a lubricating end surface, see at 60 and 62 for plugs 50 and 52, respectively and which can again further include such as a soft plastic having desired lubricating properties.

The plugs 50 and 52 are further each again constructed of a selected plasticized or composite material, such as which is differently configured from any of the previously disclosed plug designs of FIGS. 1 and 5. The plugs, again at 50 in FIG. 8, can also include an undercut and annular inner facing and perimeter defined surface 64, this assisting in seating the plug in a mating and end seating fashion relative to the inwardly recessed and cored openings defined in the existing bone 58, and which is further illustrated in FIG. 7 by receiving surfaces 65 and 67 associated with the conditioned bone end location corresponding to the installation location of the plug 50, the surfaces 65 and 67 communicating with the further recessed bored surface 54 within the bone for creating the desired cavity profile for matingly seating and engaging an identically configured portion of the composite implant. As described in preceding embodiments, the plugs 50 and 52 can be installed either singularly or in tandem and in order to provide reconditioning of the joint zone established between the bone 58 and an opposing bone (not shown).

Figure 9:
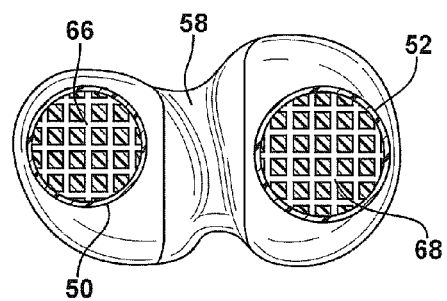
FIG. 9 is a cutaway view taken along line 9-9 of FIG. 7 and showing the configuration of the grid-shaped patterns for communicating lubricating fluid from the plugs (such as via an internal reservoir) to the externally applied cartilage layers.

FIG. 9 is a cutaway view taken along line 9-9 of FIG. 7 and showing the configuration of additional grid-shaped patterns, at 66 and 68, respectively, associated with each of the plugs 50 and 52, these again communicating lubricating fluid from the plugs (such as again via an internal reservoir) to the externally applied soft plastic/cartilage layers 60 and 62. As previously disclosed, the pluralities of tracks/patterns or passageways as shown at 66 and 68 assist in equally distributing lubricant fluid flow across an area of the plug and overlaying cartilage lubricant, this again via the communication of the lubricant through a fluid permeable matrix associated with the soft lubricant/cartilage defining layer and which assists in maintaining the desired frictionless joint environment.

Figure 10:
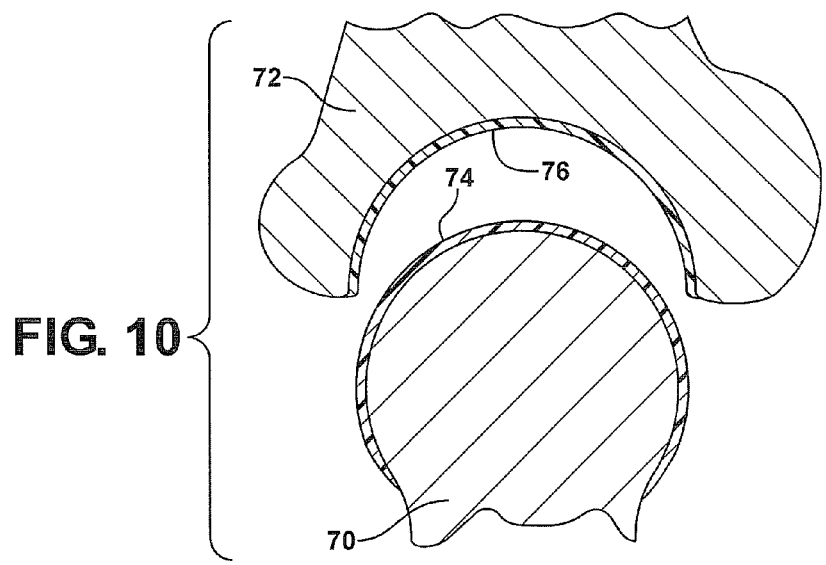
FIG. 10 is an exploded view of a further configuration of receiver and socket assembly.

FIG. 10 is an exploded view of a further configuration of a receiver 70 and socket 72 bone configuration. In particular, the configuration of FIG. 10 contemplates a minimal amount of existing bone retrofit and prior to the installation of associated and cartilage defining layers 74 and 76 for establishing a desired and substantially frictionless joint environment, this occurring such as without the requirement of a three dimensional installed implant and with the pre-requirement of sectioning the joint defining end faces associated with each of the bones 70 and 72.

Figure 11:
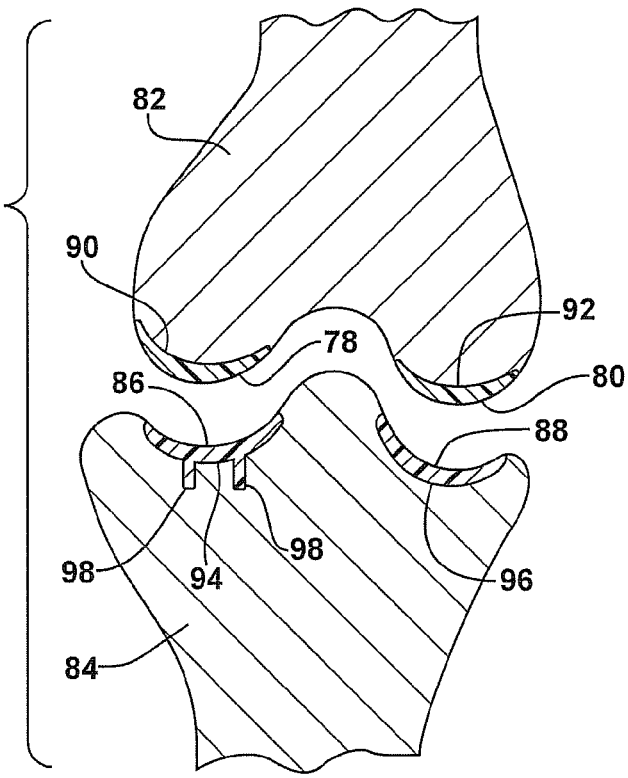
FIG. 11 is an exploded view of a still further modified configuration of joint assembly and by which a minimal resurfacing and subsequent attachment of smaller sized wear plug components, such as to contacting bone locations, provides extended life of existing bone structure.

Referring now to FIG. 11, an exploded view is shown of a still further modified configuration of joint assembly and in which minimal resurfacing of joint exposed ends of bones 82 and 84 is provided for subsequent attachment of smaller (such as arc or crescent) sized wear plug components, see at 78 & 80 for bone 82 as well as at 86 & 88 for bone 84. The wear plug components secure such as to minimally resurfaced/recessed contacting bone locations, these further being illustrated by reconditioned and recessed end surface locations at 90 & 92 (for bone 82) as well as at 94 & 96 (for bone 88), this in order to provide extended life of existing joint defined bone structure and which has not been compromised to the degree necessary to justify more extreme reconditioning as described in the various preceding embodiments.

The installation of the smaller plug or bit-sized components can be achieve through preparation of the bone end surface by cutting or other resurfacing (e.g. abrading) techniques. It is also envisioned that small drill holes, see at 98 with reference to end attached insert plug component 86, can be formed into an associated and pre-conditioned mounting location (see again at 94 for bone 84) and prior to attachment of the selected bit sized implant, e.g. again at 84 and which can further include such as rear extending mounting fasteners. It is also again understood and envisioned that appropriate adhesives and the like can be used to secure the smaller insert components securely in place.

Figure 12:
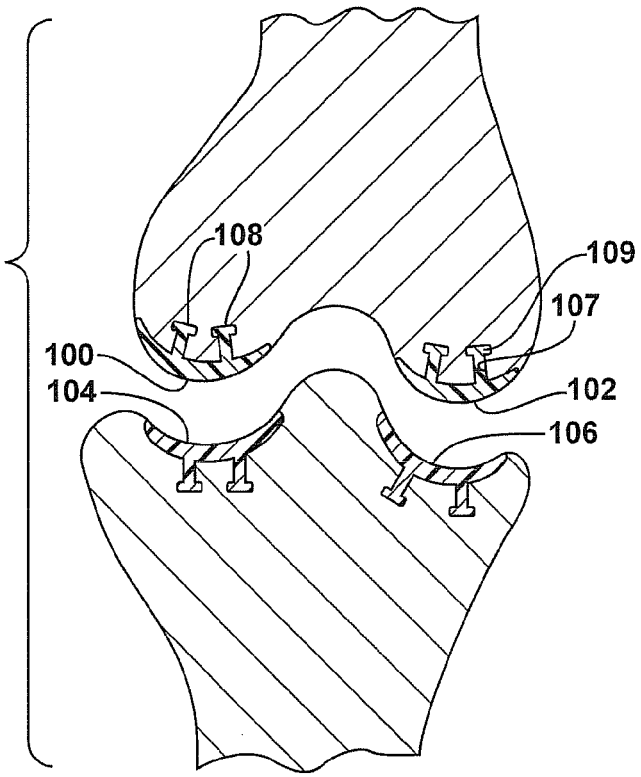
FIG. 12 is an exploded view similar to FIG. 11 and of an alternate configuration whereby end plugs are provided in the form of plasticized filling-shaped articles which are secured, via recess drill holes and associated underside fasteners extending integrally from the articles, to co-acting locations associated with each of the bones.

FIG. 12 is an exploded view similar to FIG. 11 and of an alternate configuration and whereby end plugs 100 & 102 as well as 104 & 106 are each provided in the form of plasticized filling-shaped articles. The miniaturized pseudo plug fillings each exhibit underside clips or fasteners, see as representatively identified at 108 for selected plug 100, these extending integrally from the rear mounting surfaces of each end plug article and engaging within likewise recessed machined and co-acting locations associated with each of the bones. As further shown at 107 and 109, the associated reconditioned bone end faces include an initial drill hole 107 with a further recessed and communicating undercut 109, this permitting secure and resistive inter-fit anchoring of the underside configured clips/fasteners 108 and which can again be used in combination with or separately from the application of known medical adhesives or the like.

Figure 13:
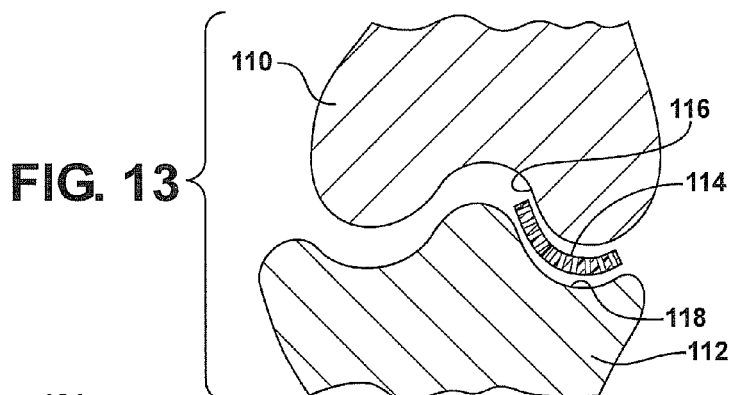
FIG. 13 an illustration of an alternate configuration of first and second bones in a joint defining relationship, and further showing a miniaturized, flexible and depth-wise apertured wear disc placed in localized inter-disposed fashion between selected coacting surfaces associated with the bones.
Figure 14:
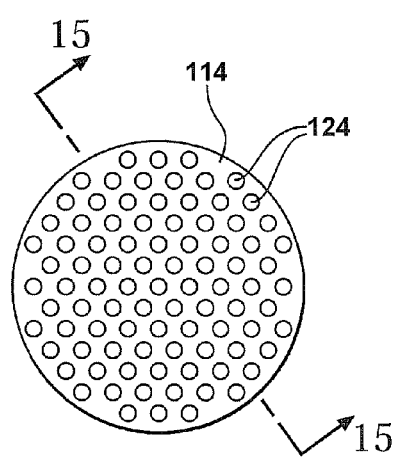
FIG. 14 is a plan view of the flexible wear disc shown in FIG. 13.

Referring to FIG. 13, an illustration is shown of an alternate configuration of first 110 and second 112 bones in a joint (such as knee joint) defining relationship. Further illustrated is the provision of a miniaturized, flexible and depth-wise apertured wear disc 114, such as which is constructed of a composite plasticized and wear-resistant material and which is placed in localized inter-disposed fashion between selected coacting surfaces, shown at 116 and 118 and associated with the bones 110 and 112. FIG. 14 is a plan view of the flexible wear disc 114 shown in FIG. 13, and which can be constructed of a soft cushioning plastic or the like.

Figure 15:
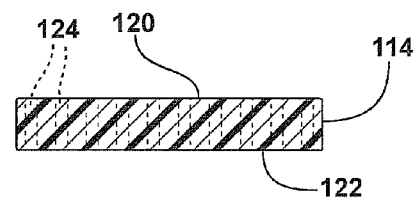
FIG. 15 is a cutaway view taken along line 15-15 of FIG. 14.
Figure 16:
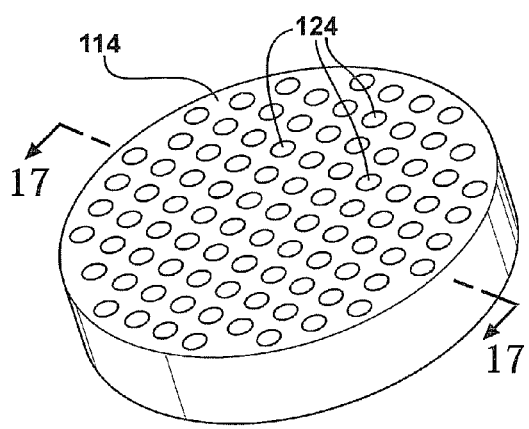
FIG. 16 is an enlarged sectional perspective of the wear disc of FIG. 13 and better illustrating the depthwise configured holes for achieving optimal lubricant fluid circulation.

As further shown in FIG. 15, a cutaway view taken along line 15-15 of FIG. 14, the wear disc 114 further evidences a plurality of depthwise extending holes or passageways 124, these intended to aggregate and uniformly distribute, across both first and second opposite surface areas (sides 120 and 122), lubricating fluid for maintaining the substantially frictionless environment of the joint region. FIG. 16 further illustrates an enlarged sectional perspective of the wear disc 114 of FIG. 13 and better illustrating the plurality of depthwise configured holes 124 for achieving optimal lubricant fluid circulation along both surfaces of the soft plastic disc 114.

Figure 17:
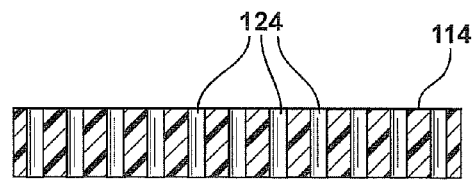
FIG. 17 is a linear slice taken from FIG. 16 and showing the spaced apart arrangement of the apertures defined in the flexible wear disc.

FIG. 17 is a linear slice taken from FIG. 16, along cutaway line 17-17, and showing the spaced apart arrangement of the apertures 124 defined in the flexible wear disc 114. The holes 124 again assist in providing enhanced fluid circulation between the sides 120 and 122 and such that the disc 114 can function as a suitable replacement for such as titanium or other metal implant materials.

Figure 18:
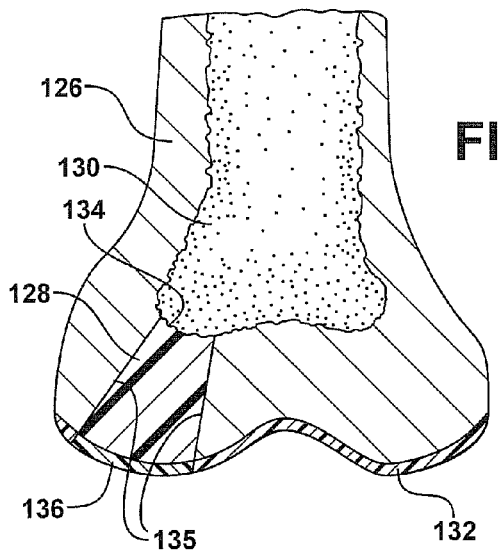
FIG. 18 is cutaway view of a selected bone according to another embodiment and which a substantially keystone shaped insert is configured for localized engagement with a selected joint end face location.

Referring now to FIG. 18, a cutaway view is shown of selected natural bone 126 according to another embodiment, and which a substantially keystone (cross sectional) or three dimensional wedge shaped composite insert 128 is configured for localized engagement with a selected joint wearing end face location. The bone 126 exhibits an interior marrow supply, at 130, and a cartilage/lubricant defined end surface 132 (and which can again be either natural or artificial softened plastic).

Figure 19:
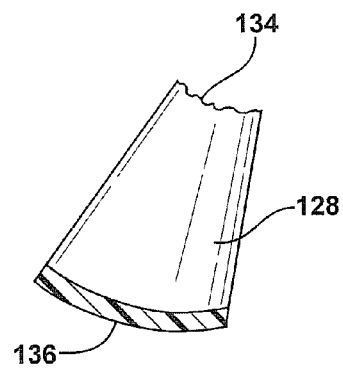
FIG. 19 is a sectional view of the composite soft plastic keystone insert of FIG. 18 and better illustrating the features of the under surface roughening (or irregularity forming) in order to promote new bone adhesion.
Figure 20:
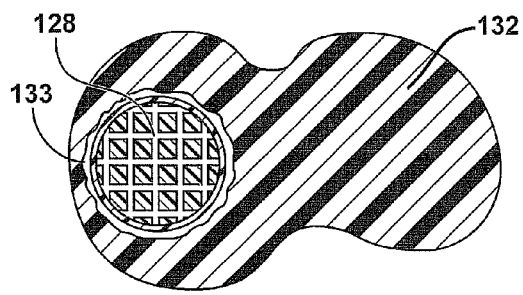
FIG. 20 is an end view of the bone illustrated in FIG. 18 with plastic keystone insert in place.

As further illustrated in the enlarged sectional view of FIG. 19 and the end view of FIG. 20, the composite soft plastic keystone insert 128 of FIG. 18 better illustrates the features of the under/inside surface roughening 134 (or irregularity forming) and in order to promote new bone adhesion once the insert 128 is installed (such as with the assistance of bonding adhesives and the like) into a previously key-stone shaped machined recess 135 defined in the joint surface of the bone 126 and further such that the roughened inner surfaces 134 are exposed to the bone marrow 130. The insert 128 further exhibits an exterior plastic surface 136, this cooperating with the cartilage defined surface 132 and consisting of either a same or similar cartilage and lubricant promoting surface.

Further shown in FIG. 20 is an end view of the bone 126 illustrated in FIG. 18 and in which a portion of the lubricant surface 132 has been removed in order to reveal the end face of the keystone insert 128. Also illustrated in FIG. 20 is the existence of a latticework pattern 133 defined in the exposed end face of the insert 128, this communicating with the lubricant surface layer 132 in order to assist in dispersing of lubricant throughout the joint zone.

Figure 21:
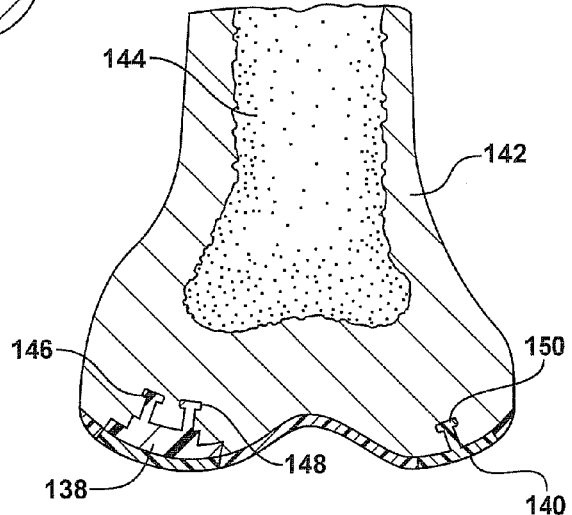
FIG. 21 is an illustration of a pair of alternately configured plastic inserts with recess mounting studs, these securing at first and second abrading joint surface locations associated with a retrofitted natural bone.

FIG. 21 illustrates a pair of alternately configured plastic inserts, see at 138 and 140, for securing to projecting end face locations associated with a bone 142 with marrow interior 144. The inserts 138 and 140 each include interiorly facing and recess mounting studs, see pair 146 and 148 associated with first insert 138 and further single stud 150 associated with second insert 140 (these being similar to the similar configured clips/fasteners identified in FIGS. 11 and 12). The inserts 138 and 140 are each further constructed of a hardened plastic (such as a composite) material and which, similar to the keystone or wedge shaped inserts, exhibit a suitable exterior face. The inserts 138 and 140 are fixedly secured to reconditioned end facing locations associated with the bone 142, such as through the engagement of the inner facing studs which secure within associated machined inner cavities (including undercut formed cavities) formed in the bone 142 and face, the studs and adjoining inner facing surfaces of the inserts securing in either or both of a press fit or suitable adhering fashion to the bone.

Figure 22:
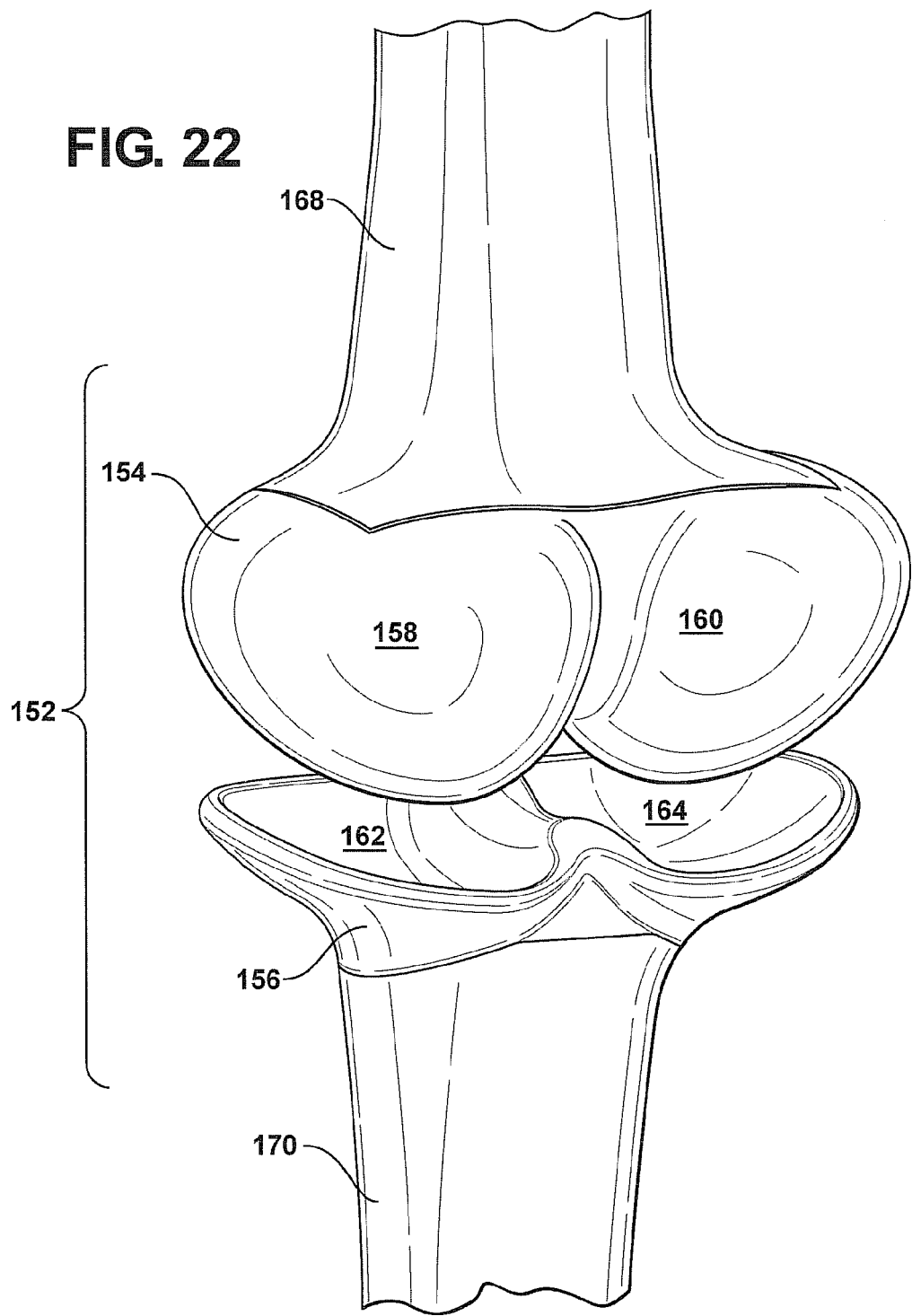
FIG. 22 is a perspective illustration of a full joint implant assembly established between male projecting/extending and female/cup-shaped receiving end secured implants, with the male and female defined ends configured to mimic the normal interaction of surfaces corresponding to such as knee joint.
Figure 23:
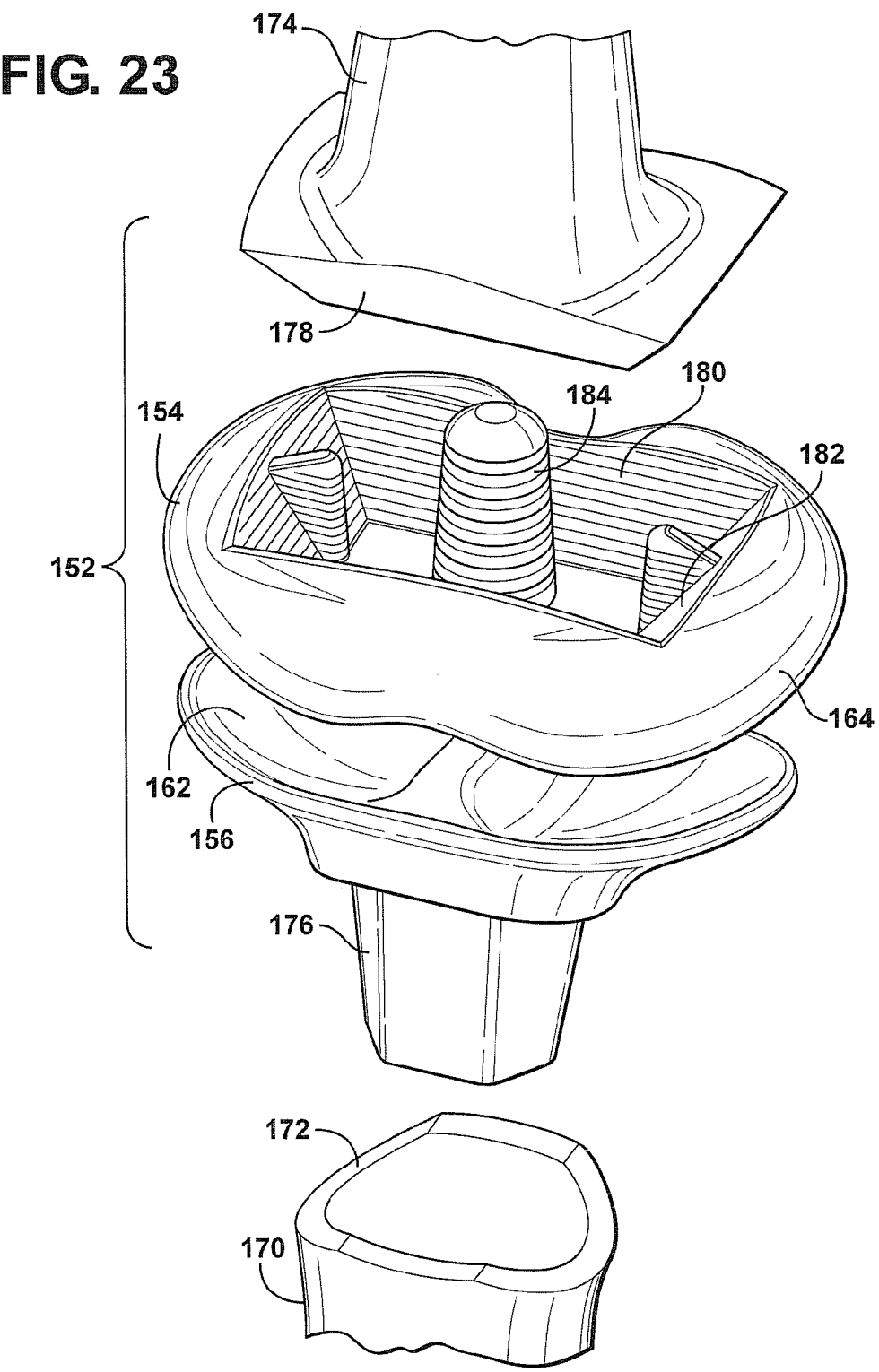
FIG. 23 is an exploded view of the joint implant assembly in FIG. 22 and illustrating a rear adhesive securing surface of a selected male insert portion, and in addition to interconnecting/transitioning stem portions, these connecting at a first end to a rear surface of either male or female implant, the stem portions being interiorly hollowed with open communicating ends configured to seat within the hollow interior of the sectioned bone ends.

Referring now to FIGS. 22 and 23 both assembled and exploded perspective illustrations are generally shown, at 152, of a full joint implant assembly and such as which is established between male projecting/extending 154 and female/cup-shaped receiving 156 end secured implants. The joint assembly corresponds in the illustrated variant to a knee assembly, it being understood that the assembly can be reconfigured for any of a hip or other joint.

The three dimensional shaped male 154 and female 156 implant portions are again constructed of any suitable material, such as not limited to a composite plastic, with the male and female defined ends configured to mimic the normal interaction of surfaces corresponding to such as the knee joint. The male implant 154 includes first 158 and second 160 generally "ball" shaped portions, these seating within mating recess cups or pockets, at 162 and 164, which are configured within opposing and seating surfaces of the female implant portion 156, this configuration assisting in preventing separation of the male and female joint halves in use with ligaments and other position maintaining structure (not shown).

The implants 154 and 156 are secured to reconditioned ends of a pair of bones 168 and 170, this further referenced in FIG. 23 by reconditioned end 172 associated with lower bone 170 for supporting female receiving implant 156. A pair of stem supporting portions, at 174 and 176, are illustrated in exploded fashion in FIG. 23, these securing to rear extending portions of the male 154 and female 156 joint defining implants and in turn seating within the hollowed interior of the bones (see in particular hollowed end of reconditioned bone 170 in FIG. 23 as well as mounted arrangement of FIG. 22 in which the stem supporting portions 174 and 176 are hidden within the bones 168 and 170. The stem portions 174 and 176 are typically constructed of a composite material, similar to that associated with the male and female joint defining implants, and include angled stem portions which are dimensioned to seat within the existing apertured interior of the existing reconditioned (end re-sectioned) bones.

The stem supporting portions, as best represented by stem 174 associated with the male implant 154, includes a pseudo tapered and polygonal/rectangular shaped mounting end, see at 178, this seating within the recess configured rear face of the selected implant 154. As best shown in FIG. 23, the rear side of the male implant 154 includes a mating and inwardly recessed taper configuration, see side walls 180 and keyed end walls 182, within which is fixedly secured the mating profile of the stem mounting end 178.

Also shown at 184 is a centrally supported and upwardly projecting anchor portion associated with the rear facing receiving cavity of the implant 154, this seating within an identically configured recess defined within the opposing interior of the stem mounting end 178 (not shown). As described previously, the use of bonding adhesives and the like are contemplated and which can assist in establishing secure bonding between the implants, associated stems and the existing bones.

Figure 24:
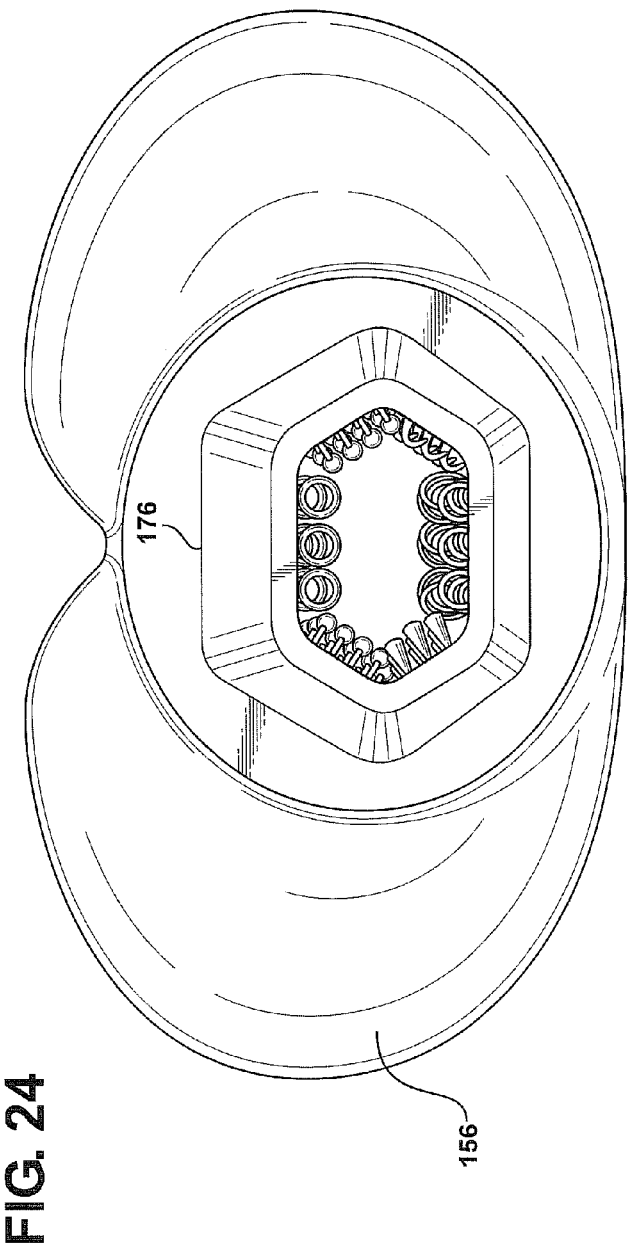
FIG. 24 is a rotated end view of a female implant and attached stem portion which is interiorly hollowed with an open communicating end configured to seat within the hollow interior of the sectioned bone end, the open interior of the stem portion further exhibiting pluralities of surface area increasing portions, such as illustrated by various types of keyed portions configured upon the open inner surfaces of the stem portions, these promoting the increase in natural bone growth and adhesion.

Additional bonding can be provided by the existing marrow of the bone (see for example FIGS. 18 and 21) promoting bone growth over and along the male/female implants, including their associated engaging stems. FIG. 24 is a rotated end view of a female implant 156 and attached stem portion B176, and which is interiorly hollowed with an open communicating end configured to seat within the hollow interior of the sectioned bone end.

Figure 25:
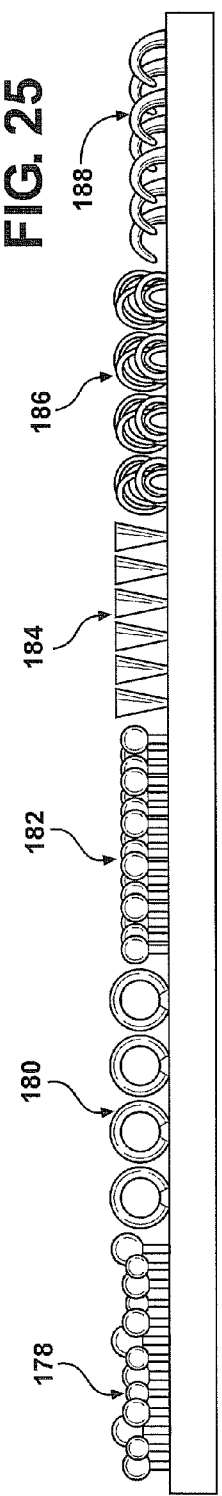
FIG. 25 is an unfolded planar view of the interconnected interior surfaces of the stem portion shown in FIG. 24 and better illustrating the varying configurations of the different types of keyed portions.

As shown, the open interior of the stem portion 176 further exhibits pluralities of surface area increasing portions, such as illustrated by various types of keyed portions 178, 180, 182, 184, 186, and 188 these being configured upon the open and interconnecting inner surfaces of the hollowed bone inserting portions of the stems, these promoting the increase in natural bone growth and adhesion through contact with the existing bone marrow. FIG. 25 is an unfolded planar view of the interconnected and communicating interior surfaces of the stem portion 176 shown in FIG. 24, and better illustrating the varying configurations of the different types of keyed portions which increase the available surface area for promoting bone growth and adhesion.

Referring now to FIG. 26, a perspective illustration is shown at 190 of a male portion associated with a partial joint assembly according to a further preferred embodiment. In this variant, a base component 192 can include an integral combination of a male implant body and bone securing stem. A further joint defining male convex portion, see at 193, can include an existing (and substantially undamaged) bone surface or can be provided as a further part of a prosthetic joint implant.

Alternatively, the stem can be separately mounted to the substrate portion of the male implant. It is also envisioned and understood that, alternative a bone secured implant, an actual bone end location can be reconditioned in order to exhibit the multi-sided and tapered configuration as illustrated by hex-shaped and interconnecting sides 194, 196, 198, et. seq.

As further shown in the rotated illustration of FIG. 27, a cap-shaped attachment, see at 200, includes a pseudo dome shaped (on convex shaped) top from which extends a threaded interior screw portion 202. The interior surface of the dome shaped top can exhibit a multi-sided configuration matching the pseudo hex shape designed into the implant 192, the screw portion 202 seating within an aperture 204 defined in a mating location of the base implant component 192. As previously described, adhesives or the like can be employed for securely bonding the cap attachment 200 to the base implant 192 and associated stem supporting portion.

Figure 28:
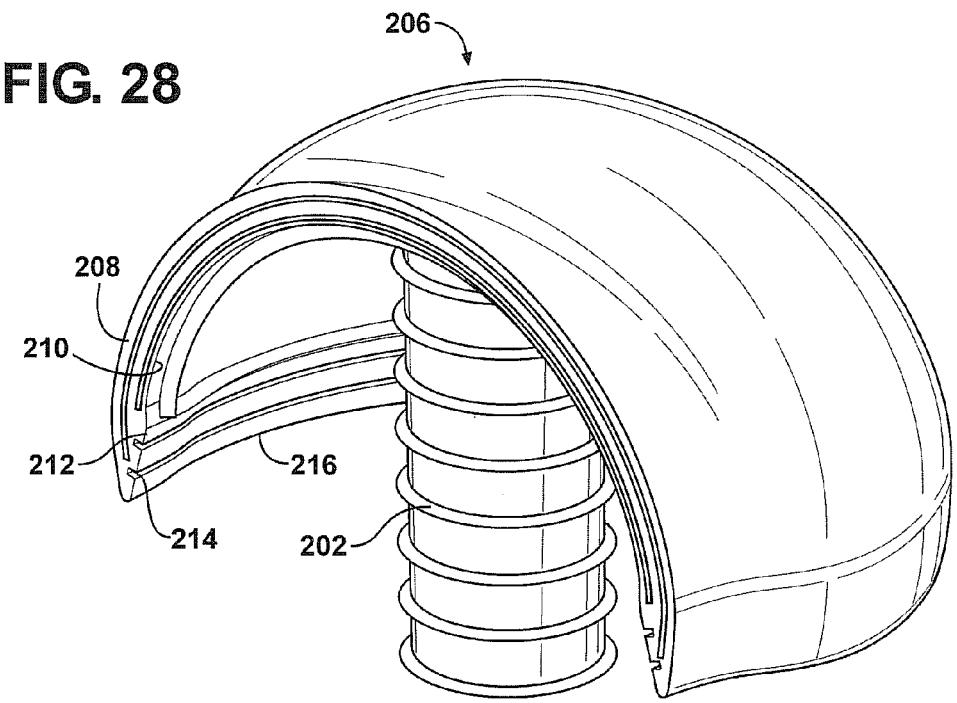
FIG. 28 is a further rotated perspective of the male implant supported cap shown in FIGS. 26 and 27.
Figure 29:
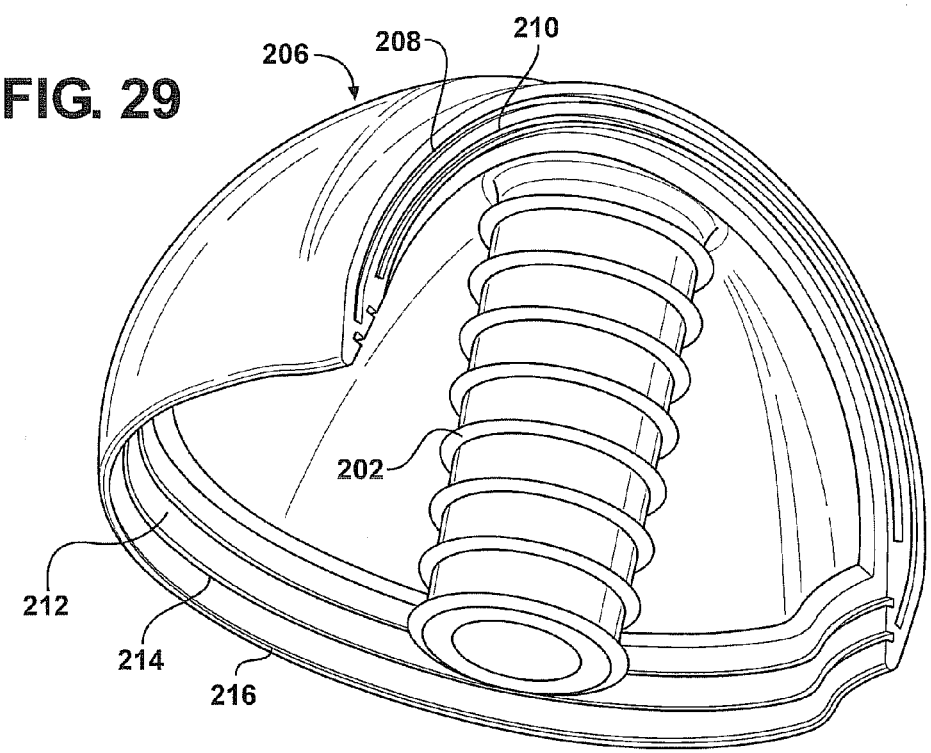
FIG. 29 is a yet further underside rotated perspective of the partial implant end cap shown in FIG. 28.

FIGS. 28 and 29 illustrate first and second rotated perspectives of a further male implant cap attachment, such as similar to that shown in FIGS. 26 and 27. The cap attachment exhibits a reinforced construction, such as which can include the provision of stiffening and/or reinforcing inserts (see at 208 and 210) incorporated into the interior wall construction of the cap attachment. The bottom extending inserts can also be removed in favor of recess notches to adjust the flexural nature of the cap attachment and it is also envisioned that the material construction of the component can be modified to exhibit different desired properties. Also illustrated are additional bottom positioned and inwardly/peripherally extending reinforcing inserts, at 212 and 214, these arranged proximate to a bottom extending edge 216 of the attachment cap. A threaded mounting screw 202 is again shown and to facilitate mounting of the cap to either an existing and reconditioned bone or a base supporting implant component as shown in FIG. 26.

Figure 30:
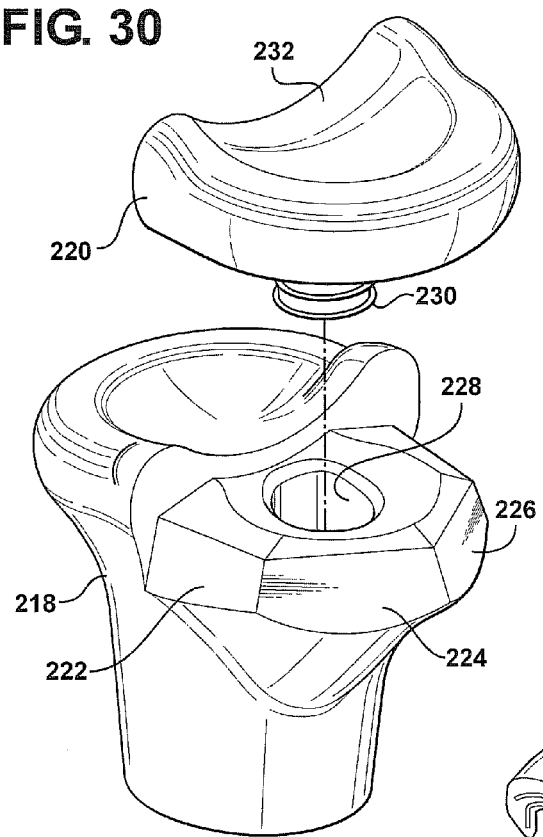
FIG. 30 is a perspective illustration of a female implant cap portion associated with a partial joint assembly, and such as which can be cooperatively established along with either a full or partial male implant assembly.
Figure 31:
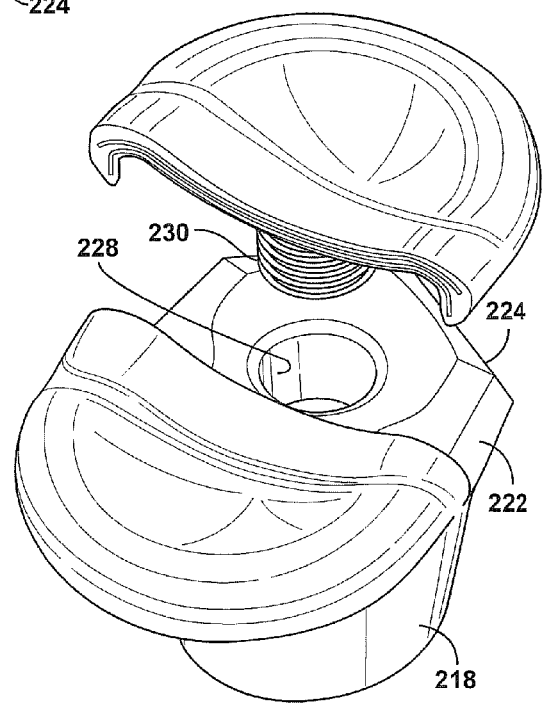
FIG. 31 is a rotated perspective of the female implant assembly of FIG. 30 and further showing a similar threaded mounting shaft for adhesive engagement with a recess defining location of a combined substrate and stem supporting portion of the female (or receiver) joint.

Referring to FIGS. 30 and 31, additional perspective illustrations are shown at 218 of a further modified substrate joint assembly and upon which is secured a configured female partial implant cap portion, further at 220, this associated with a partial joint assembly and such as which can be cooperatively established along with either a full or partial male implant assembly. The conditioning and mounting aspects illustrated are substantially identical as those described in relation to the male mounting arrangement shown in FIGS. 26 and 27, with a tapered hex pattern (sides 222, 224, 226, et. seq.) formed into an upper surface of the base component 218 and, along with an upper surface defined recess 228, seating and fixedly securing the female implant cap portion 220 and its associated and downwardly extending mounting screw portion 230.

The female cap shaped implant 220 otherwise exhibits a cup shaped top recess configuration 222 this cooperatively seating the convex shape associated with the male cap attachment (or a similar configured natural male bone joint engaging surface). Also, and with mutual reference to the male cap shaped implant 200, the current variant permits replacement of either the male or female cap shaped implant 220, such as after a given iteration of use, and without requiring concurrent replacement of the base implant component which is secured to the existing reconditioned bone.

Figure 32:
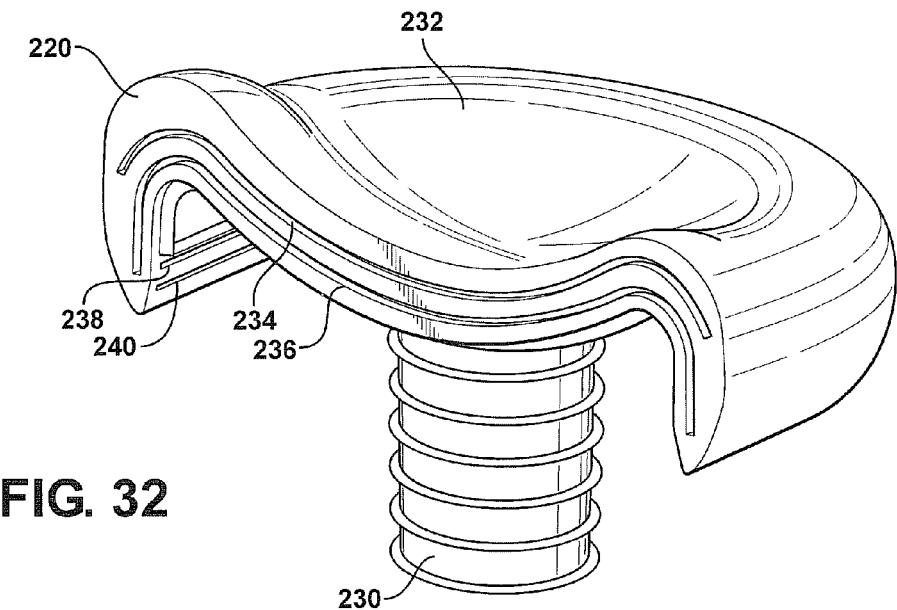
FIG. 32 is a further perspective view of the female partial implant cap of FIG. 31.
Figure 33:
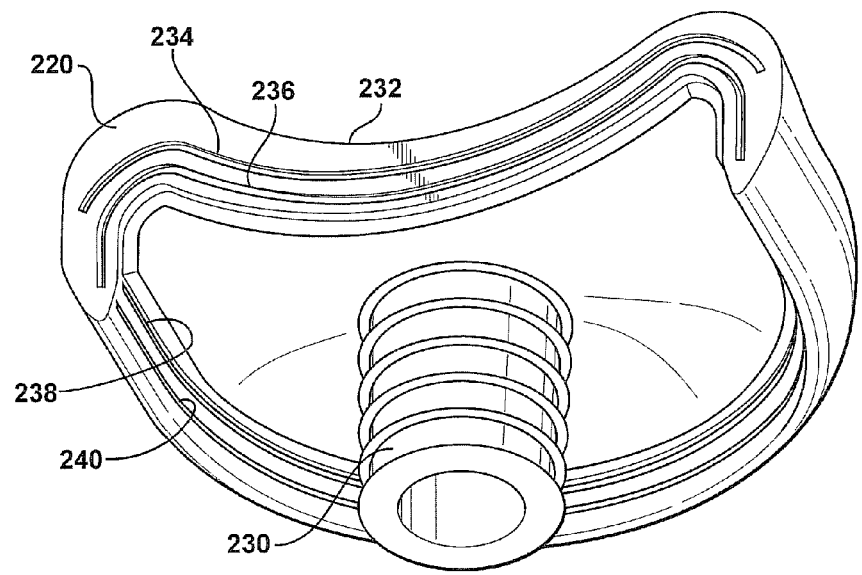
FIG. 33 is a yet further underside facing perspective view of female partial implant cap.

FIG. 31 is a rotated perspective of the female implant assembly of FIG. 30 and again showing a similar threaded mounting shaft for adhesive engagement with a recess defining location of a combined substrate and stem supporting portion of the female (or receiver) joint. Finally, FIGS. 32 and 33 are further perspective views of the female partial implant cap of FIG. 31 and which again can include stiffener inserts (see at 234, 236 and 238, 240) incorporated into the top and base perimeter walls of the cap shaped insert 220 and in order to adjust the material and flexural properties of the cap attachment.

Having described my invention, other and additional preferred embodiments will become apparent to those skilled in the art to which it pertains, and without deviating from the scope of the appended claims:

I claim:

1. An artificial joint assembly adapted for installation to preconditioned ends of first and second bones, said joint assembly comprising:

a male composite implant adapted to be secured to a preconditioned end of the first bone, said male implant exhibiting a first joint defining surface;

a female composite implant adapted to be secured to a preconditioned end of the second bone, said female implant exhibiting a second joint defining surface;

a first stem securing to a rear side of the male implant and adapted to being anchored within an interior of the first bone extending inwardly from the first preconditioned end;

a second stem securing to a rear side of the female implant and adapted to being anchored within an interior of the second bone extending inwardly from the second preconditioned end;

each of said stems further having a shaped mounting end seating within a recess configured rear face defined in each of said male and female implants;

said recess configured rear faces of said male and female implants each futher having interconnecting and inwardly tapered side walls and end walls, said end walls futher having laterally inwardly projecting keyed portions projecting into a three dimensional interior defined by said side and end walls, said shaped mounting ends of said stems each exhibiting a mating profile for engaging to said recess configured rear faces such that said interconnecting side and end walls with inwardly projecting keyed portions collectively define a mating and inwardly recessed taper configuration with which is fixedly secured said stem mounting end; and said recess configured rear faces of said implants each futher including a centrally supported and upwardly projecting anchor portion which is received within a mating recess aperture centrally defined in each of said shaped mounting ends of said stems, an open inserting end of said stems revealing an accessible interior exhibiting pluralities of surface area increasing and inwardly projecting keyed portions exhibited upon open inner surfaces of the said stem in communication with a hollowed bone interior, said keyed portions extending around an inner perimeter of said open interior surface of said stem in communication with an interior location of the bone and which are adapted to promoting an increase in natural bone growth and adhesion through contact with existing bone marrow.

* * * * *